United States Patent
Bahlmann et al.

(10) Patent No.: US 7,764,819 B2
(45) Date of Patent: Jul. 27, 2010

(54) SYSTEM AND METHOD FOR LOCAL PULMONARY STRUCTURE CLASSIFICATION FOR COMPUTER-AIDED NODULE DETECTION

(75) Inventors: Claus Bahlmann, Princeton, NJ (US); Xianlin Li, Raleigh, NC (US); Kazunori Okada, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 861 days.

(21) Appl. No.: 11/654,963

(22) Filed: Jan. 18, 2007

(65) Prior Publication Data
US 2007/0172105 A1 Jul. 26, 2007

Related U.S. Application Data

(60) Provisional application No. 60/761,927, filed on Jan. 25, 2006.

(51) Int. Cl.
*G06K 9/00* (2006.01)
(52) U.S. Cl. ...................................... 382/131
(58) Field of Classification Search ........................ None
See application file for complete search history.

(56) References Cited

OTHER PUBLICATIONS

Mario A.T. Figueiredo, et al., "Unsupervised Learning of Finite Mixture Models" IEEE Transactions on Pattern Analysis and Machine Intelligence, vol. 24, No. 3, Mar. 2002.
Kazunori Okada, et al., "*Robust Anisotropic Gaussian Fitting for Volumetric Characterization of Pulmonary Nodules in Multislice CT*" IEEE Transactions on Medical Imaging, vol. 24, No. 3 Mar. 2005.
Claus Bahlmann, "*Directional Features in Online Handwriting Recognition.*" Pattern Recognition 39 (2006) 115-125.

*Primary Examiner*—Charles Kim
(74) *Attorney, Agent, or Firm*—Donald B. Paschburg; F. Chau & Associates, LLC

(57) ABSTRACT

A method for classifying pulmonary structures in digitized images includes providing approximate target structure locations of one or more target structures in a digitized 3-dimensional (3D) image, fitting an anisotropic Gaussian model about said approximate target locations to generate more precise 3D target models and center locations of said one or more target structures, warping each said 3D target model into a 3D sphere, constructing a bounding manifold about each said warped 3D sphere, and identifying clusters on said bounding manifold wherein said one or more target structures are classified.

24 Claims, 10 Drawing Sheets

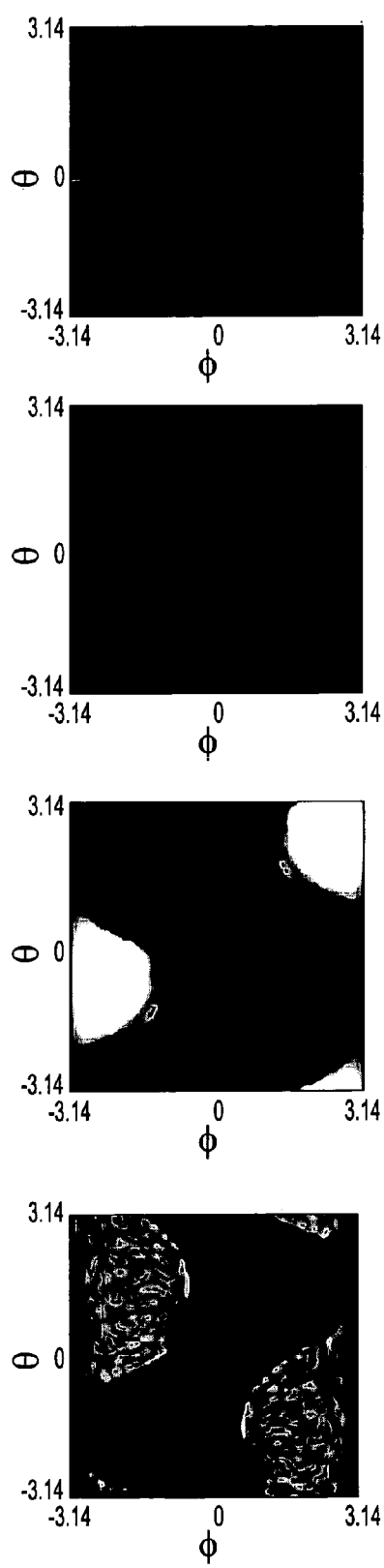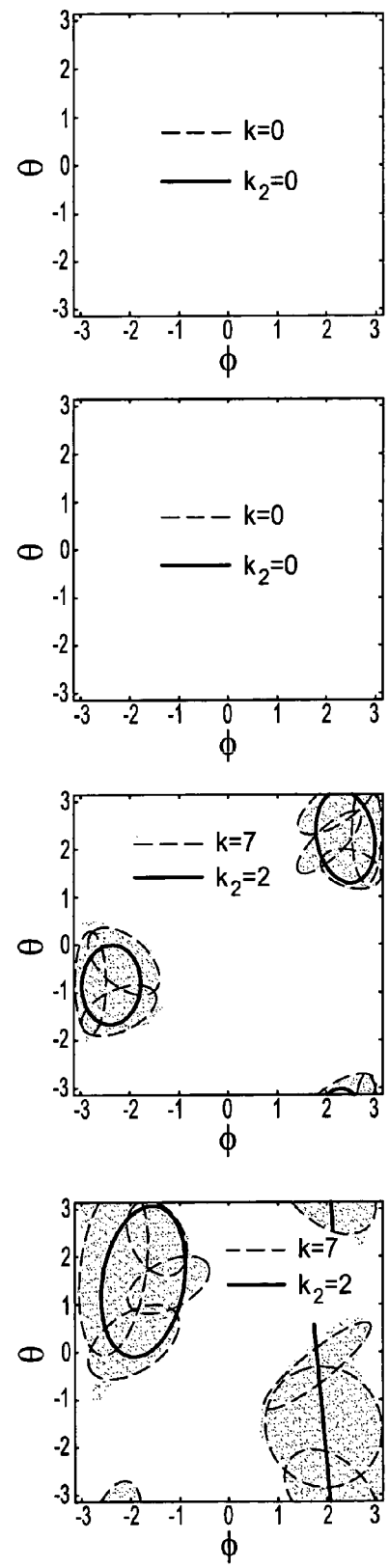
FIG. 4(c)  FIG. 4(d)

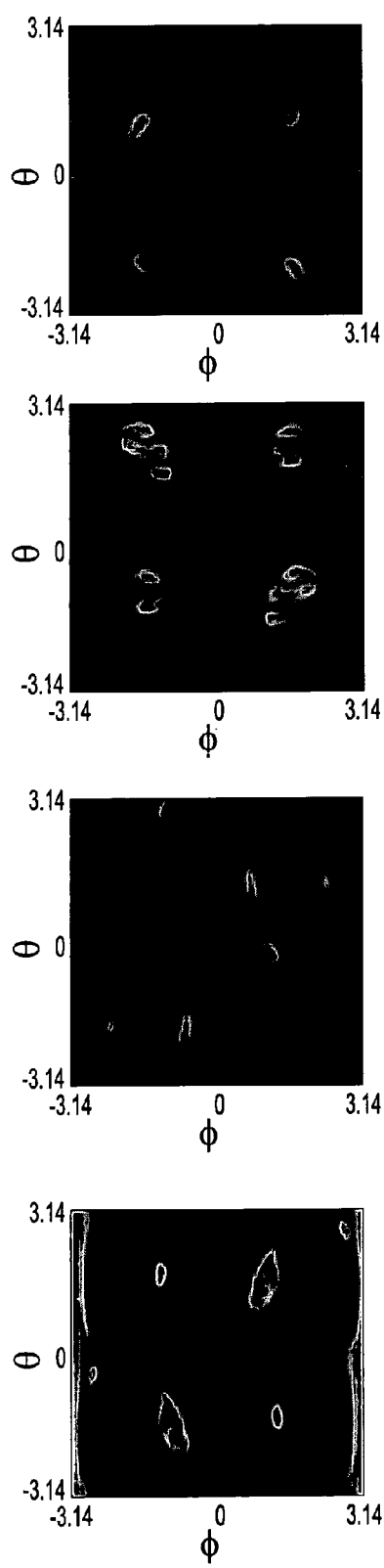
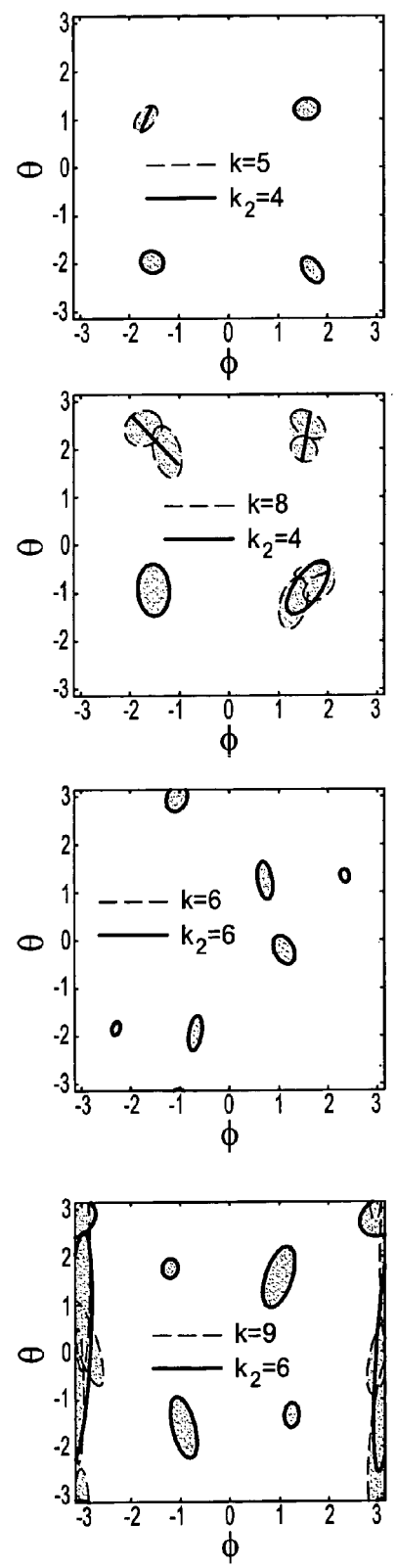
FIG. 5(c)  FIG. 5(d)

SYSTEM AND METHOD FOR LOCAL PULMONARY STRUCTURE CLASSIFICATION FOR COMPUTER-AIDED NODULE DETECTION

CROSS REFERENCE TO RELATED UNITED STATES APPLICATIONS

This application claims priority from "Local Pulmonary Structure Classification for Computer-Aided Nodule Detection", U.S. Provisional Application No. 60/761,927 of Bahlmann, et al., filed Jan. 25, 2006, the contents of which are incorporated herein by reference.

TECHNICAL FIELD

This invention is directed to the classification of local structure types in digitized medical images.

DISCUSSION OF THE RELATED ART

Lung cancer is responsible for over 160,000 deaths in the past year in the United States alone. While not smoking is the best prevention against lung cancer, early detection is the key to improving patient prognosis. When the cancer is detected early and surgery is performed, the 5-year survival rate for patients with stage I non-small-cell lung cancer is 60% to 80%. However, patients who do not have surgery face a 5-year survival rate of only 10%. 1

Imaging techniques such as computer tomography (CT) scans offer noninvasive and sensitive approaches to early detection. Computer-aided detection and diagnosis (CAD) of lung nodules in thoracic CT scans decreases the possibility of human error for a more efficient and standardized diagnostic process. In CT scans, lung nodules appear as dense masses of various shapes and sizes. They may be isolated from or attached to other structures such as blood vessels or the pleura.

Recently a number of techniques have been proposed for automated detection and classification of nodules in thin-slice CT including region growing and automatic threshold determination, template matching with Gaussian nodule models, using 3D nodule selective and noise suppressing filters, nodule matching, and deformable geometrical and intensity templates. However, a shortcoming of these state of the art CAD systems is differentiating between nodules and other dense structures such as blood vessels. Due to the circular-shape assumptions used in most of the systems, curved vessels and their junctions are often incorrectly detected as nodules, resulting in false positive (FP) cases.

To reduce the number of such FPs, two types of solutions have been proposed previously: correlation-based filters to enhance the area of interest with fuzzy shape analysis for vessel tree reconstruction, and utilizing tracking of vessel medial axes given by Hessian-based analysis. The drawbacks of the former approach include its inflexibility. Simple structural templates used in the study will not handle many complex vascular shapes and topologies. On the other hand, the latter approach is computationally very expensive while being able to handle more irregular structures.

SUMMARY OF THE INVENTION

Exemplary embodiments of the invention as described herein generally include methods and systems for classifying local structure types, such as nodules, vessels, and junctions, in thoracic CT scans. This classification is useful for the computer aided detection (CAD) of lung nodules, and can be used as a post-process component of any lung CAD system so as to reduce false positives (FPs) caused by the vessels and junctions. This classification thus assumes that positive candidates are provided by such a CAD system or from radiologist's report, focusing on the problem of FP reduction. In such a scenario, the classification results provide an effective means of removing false positives caused by vessels and junctions thus improving overall performance.

A method according to an embodiment of the invention transforms the classification of various 3D topological structures into much simpler 2D data clustering classification, to which more generic and flexible solutions are available in literature, and which is better suited for visualization. Apart from the computational benefits, such an approach has the advantage of a more generic and flexible inventory of analysis techniques and more illustrative visualization potentiality, which is useful in the context of a possible interaction with the radiologist.

Given a nodule candidate, first, an anisotropic Gaussian is robustly fit to the data. The resulting Gaussian center and spread parameters are used to affine-normalize the data domain so as to warp the fitted anisotropic ellipsoid into a fixed-size isotropic sphere. An automatic method can extract a 3D spherical manifold, containing the appropriate bounding surface of the target structure. Scale selection is performed by a data driven entropy minimization approach. The manifold is analyzed for high intensity clusters, corresponding to protruding structures, using techniques such as EM-clustering with automatic mode number estimation, directional statistics, and hierarchical clustering with a modified Bhattacharyya distance. The estimated number of high intensity clusters explicitly determines the type of pulmonary structures: nodule (0), attached nodule (1), vessel (2), junction (>3). A method according to an embodiment of the invention extends a Gaussian fitting method, including automatic mode number selection, with the use of directional statistics, in particular a multivariate wrapped Gaussian modeling.

Beyond the scope of lung CAD, a classification method according to an embodiment of the invention can be used to provide meaningful information of vascular structures in various domains such as angiography. This local procedure is more flexible and efficient than current state of the art and will help to improve the accuracy of general lung CAD systems. Further, volume-of-interest (VOI) representations chosen in the parts of the modeling have beneficial visualization capabilities, such as the unwrapped 2D bounding manifold, which aids user (radiologist) interaction.

A qualitative study for selected examples of thoracic CT images demonstrated favorable classification results in this domain. An algorithm according to an embodiment of the invention can robustly classify examples of nodules, attached nodules, vessels and vessel junctions.

According to an aspect of the invention, there is provided a method for classifying pulmonary structures in digitized images, including providing approximate target structure locations of one or more target structures in a digitized 3-dimensional (3D) image, fitting an anisotropic Gaussian model about each said approximate target locations to generate more precise 3D target models and center locations of said one or more target structures, warping each said 3D target models into a 3D sphere, constructing a bounding manifold about each said warped 3D sphere, and identifying clusters on said bounding manifolds wherein said one or more target structures are classified.

According to a further aspect of the invention, the digitized image comprises a plurality of intensities corresponding to a domain of points on a 3-dimensional grid.

According to a further aspect of the invention, fitting an anisotropic Gaussian model about an approximate target location comprises using Gaussian scale-space mean shift analysis and Jensen-Shannon divergence-based automatic bandwidth selection generating a 3D ellipsoidal model of said target structure, wherein the center and dimensions of said 3D ellipsoid correspond to the center and covariances of said Gaussian model.

According to a further aspect of the invention, warping said 3D target model comprises affine-normalizing said 3D ellipsoid wherein scaling directions and factors are obtained from the structure covariance of said anisotropic Gaussian model.

According to a further aspect of the invention, constructing a bounding manifold further comprises unwrapping the 3D surface of the warped sphere into a 2D representation, and determining a radius of an appropriate bounding manifold.

According to a further aspect of the invention, unwrapping the 3D surface of the warped sphere into a 2D representation comprises transforming the surface of said warped sphere into spherical coordinates $(\theta, \phi)$ wherein $\phi \in [-\pi, \pi]$ and $\theta \in [-\pi, \pi]$.

According to a further aspect of the invention, determining a radius of an appropriate bounding manifold comprises constructing a plurality of spherical manifolds of different radii about said warped sphere, unwrapping each spherical manifold into a 2D representation, normalizing the intensity value distribution on each said unwrapped spherical manifold, calculating an intensity entropy for each said unwrapped spherical manifold wherein intensity values are treated as probability values wherein an entropy distribution is defined, and finding a radius that minimizes said entropy distribution.

According to a further aspect of the invention, identifying clusters comprises using an expectation-maximization to fit a mixture $$N_w(\Theta) = \sum_{p=1}^{P} c_p N_w^p(\Theta)$$

of multivariate wrapped Gaussian distributions $N_w^p(\Theta)$ of a vector variable $\Theta = (\vartheta_1, \ldots, \vartheta_F)^T$ to objects protruding through said bounding manifold subject to a minimum description length criterion, wherein mixture component probabilities $c_p$ are estimated within the expectation-maximization, wherein in each dimension $\vartheta_i$ satisfies $\vartheta = x_w = x \mod 2\pi \in (-\pi, \pi]$, $N_w^p(\Theta)$ satisfies $$N_w^p(\Theta) = \sum_{k_1=-\infty}^{\infty} \ldots \sum_{k_F=-\infty}^{\infty} N^p(\Theta + 2\pi k_1 e_1 + \ldots + 2\pi k_F e_F),$$

wherein $e_k = (0, \ldots, 0, 1, 0, \ldots, 0)^T$ is the $k^{th}$ Euclidean basis vector, with an entry of 1 at the $k^{th}$ element and 0 elsewhere, wherein estimates $\hat{\mu}_\Theta^p$ and $\hat{\Sigma}_\Theta^p$ of a mixture component p are obtained within the expectation-maximization from a sample set $X = \{\vartheta^{(1)}, \ldots, \vartheta^{(M)}\}$ based on a directional mean $$(\hat{\mu}_\vartheta)_f = \arg\left(\frac{1}{M} \sum_{m=1}^{M} \exp(i\vartheta_f^{(m)})\right)$$

and covariance $$\hat{\Sigma}_\vartheta = \frac{1}{M-1} \sum_{m=1}^{M} \Theta^{(m)'} \Theta^{(m)'T}$$

with $$\vartheta^{(m)'} = \left(\vartheta_f^{(m)} - (\hat{\mu}_\vartheta)_f\right) \mod 2\pi,$$

and wherein observations X are drawn directly from a 2D unwrapped image $I(\theta, \phi)$, where the number of occurrences of each sampled $(\theta_m, \phi_m) \in (-\pi, \pi] \times (-\pi, \pi]$ is set proportional to a corresponding image matrix value $I(\theta_m, \phi_m)$.

According to a further aspect of the invention, the method comprises using agglomerative hierarchical clustering to merge clusters within a predefined distance of each other, using a distance metric for a pair of multivariate wrapped Gaussian distributions equivalent to $$\frac{1}{8}((\mu_2 - \mu_1)\mod 2\pi)^T \left(\frac{\Sigma_1 + \Sigma_2}{2}\right)^{-1} ((\mu_2 - \mu_1)\mod 2\pi) + \frac{1}{2}\ln\frac{|\Sigma_1 + \Sigma_2|}{\sqrt{|\Sigma_1||\Sigma_2|}},$$

wherein $\mu_1$ and $\mu_2$ are the mean values of the pair of Gaussian distributions, and $\Sigma_1$ and $\Sigma_2$ are their respective variances.

According to a further aspect of the invention, the pulmonary structure class is determined by the number of wrapped Gaussian component clusters associated with a target structure, wherein a solitary nodule has 0 clusters, an attached nodule has 2 clusters, a vessel has 4 clusters, and a vessel junction has 6 or more clusters.

According to another aspect of the invention, there is provided a program storage device readable by a computer, tangibly embodying a program of instructions executable by the computer to perform the method steps for classifying pulmonary structures in digitized images.

BRIEF DESCRIPTION OF THE DRAWINGS

FIGS. 4(a)-(d) and 5(a)-(d) depict illustrative examples of a pulmonary structure classification method of an embodiment of the invention for thoracic CT scans.

DETAILED DESCRIPTION OF THE PREFERRED EMBODIMENTS

Figure 1:
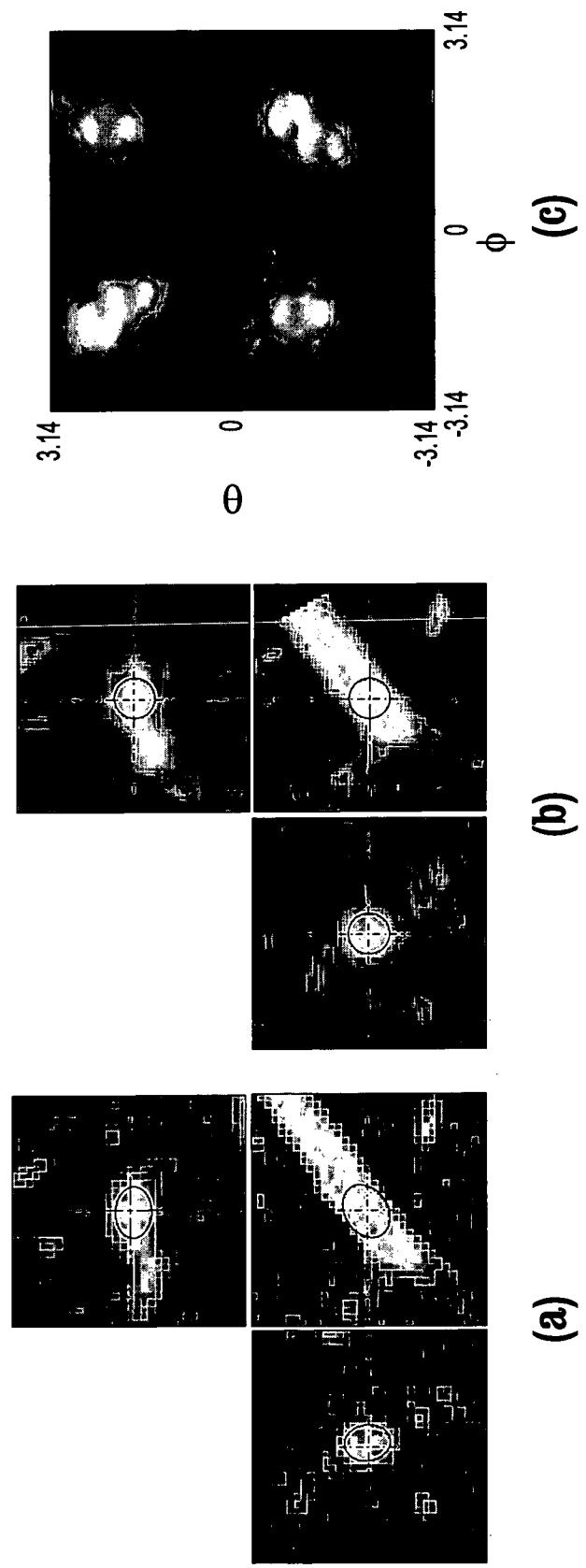
FIGS. 1(a)-(c) illustrate a method for pulmonary structure classification, according to an embodiment of the invention.

Exemplary embodiments of the invention as described herein generally include systems and methods for classifying local structure types in thoracic scans. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A classification system according to an embodiment of the invention includes (1) a module for anisotropic Gaussian fitting, (2) a construction of a 2D manifold at the boundary of the pulmonary structure, and (3) a robust cluster analysis of this manifold. Part (2) uses a data driven scale selection based on entropy minimization. Part (3) uses statistical analysis methods, such as expectation-maximization (EM)-based clustering with automatic mode number selection, directional data modeling, and hierarchical clustering based on a variant of the Bhattacharyya distance. The number of high intensity clusters in this analysis will directly determine the pulmonary structure class. Unlike other global methods such as vessel tree reconstruction, this method allows for the localized flexible examination of pulmonary structures.

In the setting of a nodule detection application, incorrectly detected and segmented vessel and vessel branch structures represent a false positive (FP) case. A classification method according to an embodiment of the invention rejects all such non-nodule structures, and, as a byproduct, to infer the category of the type of pulmonary structure under consideration, that is, nodule, attached nodule, vessel, or vessel junction. Furthermore, a classification solution according to an embodiment of the invention can serve as a post-process filter within a lung CAD system so as to reduce FPs caused by the vessels and junctions.

Figure 7:
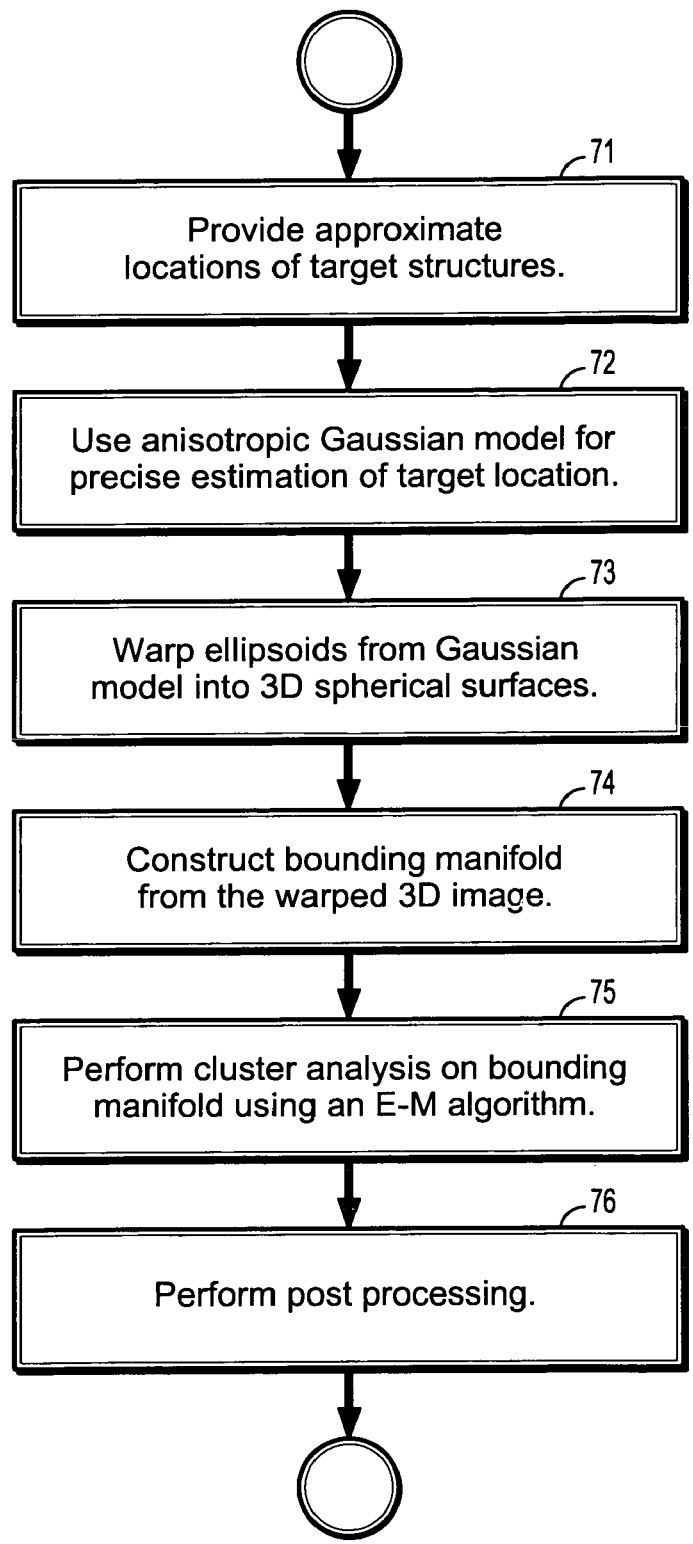
FIG. 7 is a flowchart of classification method according to an embodiment of the invention.

A flowchart of a pulmonary classification method according to an embodiment of the invention is presented in FIG. 7. A method according to an embodiment of the invention assumes that approximate locations of pulmonary structures are present, for instance, from a CAD system, a radiologists manual reading, or reports, etc. A one-click nodule segmentation algorithm can be used to locate and segment target structures including nodules, attached nodules, vessels, and vessel junctions. Referring now to the figure, nodule candidate locations, provided a priori at step 71, serve as initialization to this semi-automatic segmentation solution. At step 72, an anisotropic Gaussian model is fit to the target structure intensities, yielding more precise 3D ellipsoidal models of the targets. These ellipsoids are warped into 3D spheres at step 73. Bounding manifolds are constructed from the warped 3D spheres at step 74. According to an embodiment of the invention, this construction includes unwrapping the 3D surface of the spheres into a 2D spherical coordinate representation, followed by determining a radius of an appropriate bounding manifold. Cluster analysis of the bounding manifold is performed at step 75, followed by post-processing at step 76. Details of these steps are described below.

Referring to step 72, an algorithm according to an embodiment of the invention is based on robustly fitting an anisotropic Gaussian-based intensity model to the data using Gaussian scale-space mean shift analysis and Jensen-Shannon divergence-based automatic bandwidth selection. These techniques provide a precise estimate of target center from imprecise CAD or manual initialization. An ellipsoidal manifold in 3D is extracted from the target structure boundary. Ellipsoid fitting is usually non-trivial, however, this task is alleviated by the choice of the local structure segmentation, which gives accurate estimates of center and ellipsoidal shape of the nodule in terms of the Gaussian parameters mean and covariance. The robustness of this estimation also allows segmentation of non-nodule areas such as vessels and vessel junctions/branches of interest.

In order to simplify the mathematical representation, the original volume of interest (VOI) is affine-normalized at step 73. This involves warping the VOI to transform the segmented anisotropic ellipsoid into a fixed-sized isotropic sphere, placed at the center of the VOI. The parameters of the affine-normalization, that is, scaling directions and factors, can be straightforwardly obtained from an eigenvalue analysis of the structure covariance estimated by the segmentation module.

FIGS. 1(a)-(c) illustrate an exemplary pulmonary structure classification, according to an embodiment of the invention. FIG. 1(a) shows the original volume of interest (VOI) and segmented nodule candidate, with an ellipsoid fitted nodule structure, here a vessel. The ellipsoid fitting is obtained from the anisotropic Gaussian fitting module. FIG. 1(b) represents an affine normalization of the original VOI, in that the ellipsoid is warped to an isotropic sphere. FIG. 1(c) represents a bounding manifold of the segmented structure at distance $r_{bound}$, unwrapped to a 2D image and parameterized by the spherical polar coordinates $\theta$ and $\phi$. The image grayscale values were obtained via tri-linear interpolation.

Referring again to FIG. 7, the category of the type of pulmonary structure under consideration is determined at step 74 by a cluster analysis of an appropriate manifold, computed from the bounding area of the target structure. A spherical manifold according to an embodiment of the invention is constructed from the affine-normalized 3D image. Geometrically, it is aimed to represent a spherical layer slightly beyond the target structure bounding surface, such that it contains information about protruding objects passing through the surface. Its shape is assumed ellipsoidal in the original VOI, in particular, proportional to the ellipsoid obtained from the anisotropic Gaussian-based segmentation. Hence, in the affine-normalized representation it corresponds to an isotropic spherical shape as well, defined by the center point ($a_{bound}$, $b_{bound}$) and radius $r_{bound}$. Whereas the center point is identical with the one of the segmented ellipsoid, the spherical radius $r_{bound}$ will be determined in a data driven way, explained below.

Assuming a fixed $r_{bound}$, the bounding manifold representation can be transformed from Cartesian (x, y, z) to the spherical coordinates (θ, φ). Here, θ refers to the azimuth, and φ to the polar angle. The result is an "unwrapped" representation of the affine-normalized ellipsoid as a 2D image matrix I(θ, φ). FIG. 1(c) illustrates the result for pulmonary structure example. Note that, contrary to common convention, the polar angle ranges over an interval of $Interval_\phi = 2\pi$ (instead of π), that is, φ∈[−π,π], resulting in a double occurrence of the Cartesian voxels. The reason for introducing this redundancy is that clustering, which will be introduced below, requires a periodic behavior of I(θ, φ) in both parameters over their respective intervals $Interval_\theta$ and $Interval_\phi$, that is, I(θ+$Interval_\theta$, φ+$Interval_\phi$)=I(θ, φ). For the case of spherical coordinates, this is obviously not fulfilled if $Interval_\phi = \pi$.

According to an embodiment of the invention, the determination of the appropriate radius $r_{bound}$ uses a data driven approach, based on the entropy of the intensity distributions. To motivate this approach, consider FIGS. 2(a)-(f), each of which illustrates the unwrapped ellipsoid representation in the (θ, φ)-domain with different radii r, as indicated in the figures. FIG. 2(g) shows the respective image histogram entropy $E_r$, computed on image intensities, for radii r∈{1, . . . , 32}. An exemplary image entropy can be computed from the image intensities I(θ, φ) according to $$E = -\sum_{\theta,\varphi} \left( \frac{I(\theta, \varphi)}{\sum_{\theta',\varphi'} I(\theta', \varphi')} \right) \times \log\left( \frac{I(\theta, \varphi)}{\sum_{\theta',\varphi'} I(\theta', \varphi')} \right).$$

Figure 2:
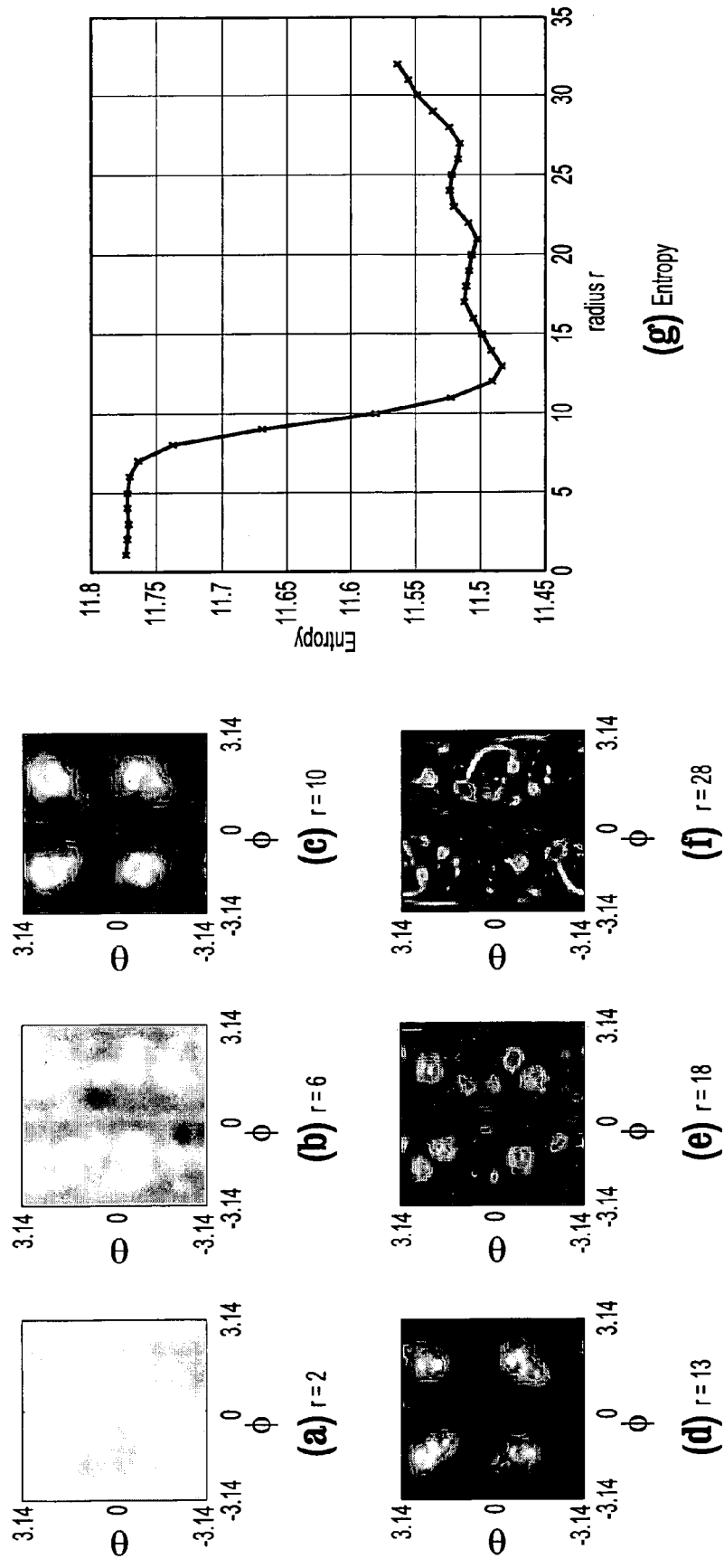
FIGS. 2(a)-(g) depict the effects of unwrapped ellipsoids of different radii r and the respective image intensity histogram entropy, according to an embodiment of the invention.

The unwrapped manifold image is treated as a 2D likelihood function after normalizing the image intensity value distribution appropriately. Then intensity entropy is computed directly with the normalized intensity values interpreted as probability values. Radius selection involves automatically choosing a radius such that high intensity clusters, due to protruding structures, appear most distinctively in the corresponding manifold. Such a manifold image, consisting of a few clusters as shown in FIG. 2(d), should have lower entropy than images with smaller and larger radii due to the following intuitive arguments. The smaller radii makes the corresponding bounding ellipsoids go through inside target structures, resulting in high entropy values with more flat likelihoods as shown in FIGS. 2 (a)-(b). On the other hand, the larger radii also causes high entropy due to appearance of other "non-target" structures located nearby as shown in FIGS. 2(e)-(f). Therefore the appropriate radius $r_{bound}$ forms a local minimum of the entropy distribution $E_r$. In this respect, $r_{bound}$ is chosen to be located at the first appearance of a positive difference quotient $$\frac{\Delta E_r}{\Delta r},$$

that is, $$r_{bound} = \min_r \{r \,|\, E_{r+1} > E_r\}.$$

Having transformed parts of the 3D pulmonary structure to a 2D image, one can apply well-studied, efficient, and easily visualizable 2D image analysis techniques. As can be seen from FIG. 1(c), the bounding manifold contains valuable information for pulmonary structure classification. In fact, the number of high intensity clusters exposes the type of the pulmonary structure, being equivalent to the number of protruding objects passing through the defined boundary. A classification of an embodiment of the invention builds upon this observation, having the following domain assumptions in mind:

0 clusters in the bounding manifold indicate a lack of connected adjacent structure, hence, the segmented structure corresponding to a solitary nodule;

1 cluster in the bounding manifold indicates a single connection to an attached structure, which in many cases originates from a nodule attached to larger structures, like the lung wall, etc.;

2 clusters indicates two connections, which is most often observed for blood vessels; and >3 clusters indicate a vessel junction.

According to an embodiment of the invention, the number of high intensity clusters is identified through a clustering analysis, performed at step 75 of FIG. 7. A clustering strategy of an embodiment of the invention is based on an expectation-maximization (EM)-based fitting of Gaussians. In addition to the standard EM Gaussian clustering properties, a clustering algorithm of an embodiment of the invention needs to reflect the continuities in the (θ, φ)-domain that appear at the edge of the 2D bounding manifold image. In particular, a bounding manifold representation parameterized by the spherical angular variables (θ, φ) corresponds to directional data. For an illustration of directional data, consider the simplified illustration of FIG. 3. An appropriate clustering algorithm in the directional (θ, φ)-domain should recover a single cluster. However, with a linear instead of directional modeling, each of the three observable structures would form an independent cluster. Furthermore, clustering algorithm of an embodiment of the invention should be able to automatically determine the number of modes.

Directional data may be visualized as points on the surface of a hypersphere, in two dimensions on the circumference of a circle. FIGS. 6(a)-(b) illustrate examples of directional data. A situation that arises with directional data is as follows. For a circular variable θ, an addition "a+b" becomes "(a+b)mod 2π", where angles are represented in the interval (−π, π]. Note that under this assumption the mod operator also maps to (−π, π]. Let the variables $\mu_\vartheta^c$ and $V_\vartheta^c$ denote the circular counterparts of mean and variance. Reasonable definitions for $\mu_\vartheta^c$ and $V_\vartheta^c$ should remain invariant under a shift of the zero direction which is expressed by $\tilde{\vartheta} = (\vartheta - v) \mod 2\pi$. The invariances for a circular variable should be $$\mu_{\tilde{\vartheta}}^c = (\mu_\vartheta^c - v) \mod 2\pi,$$

$$V_{\tilde{\vartheta}}^c = V_\vartheta^c.$$

Figure 6:
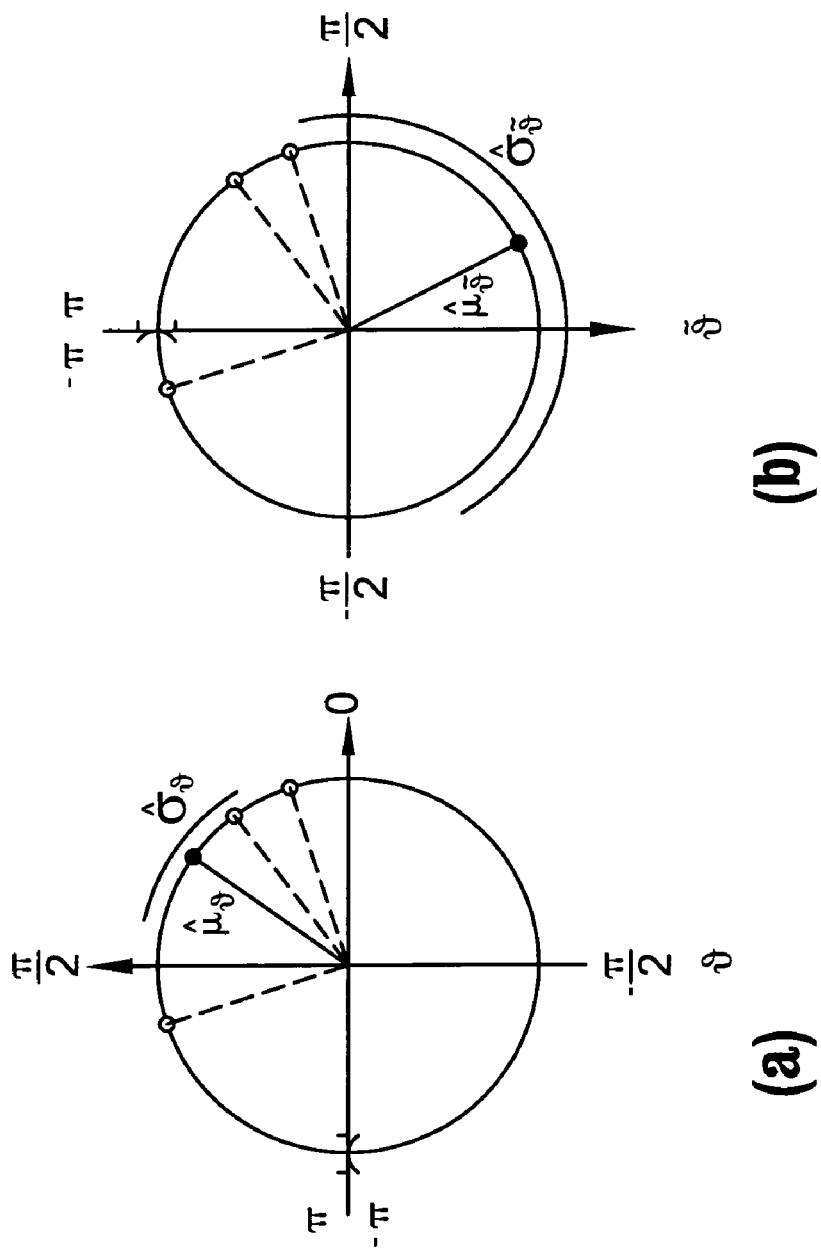
FIGS. 6(a)-(b) illustrate examples of directional data, according to an embodiment of the invention.

However, it can easily be verified from the example in FIG. 6 that the desired invariance is violated. FIG. 6 depict a simple set of circular observations, with Θ={0.1π,0.2π,0.6π} in FIG. 6(a), and $\tilde{\Theta}$={0.6π,0.7π,−0.9π} in FIG. 6(b), which corresponds to v=−0.5π. For these observations, unbiased maximum likelihood (ML) estimates for mean and variance can be computed to $\hat{\mu}\vartheta$=0.3π, $\hat{\sigma}\vartheta$≈0.26π, $\hat{\mu}\vartheta$≈0.13π, and $\hat{\sigma}\vartheta$≈0.90π, which obviously violate shift invariance. In the figures, values of mean and variance are illustrated by the location of the black dot and the length of the accompanying arc, respectively. Thus, for circular data the linear definitions of mean and variance are highly dependent on the zero direction, which is an inappropriate behavior and demands for a suitable handling.

To handle this situation, assume a circular random variable $\theta$ with a PDF $p(\theta)$. In agreement with standard statistical properties, the PDF should satisfy $p(\theta) \geq 0$ and $$\int_{-\pi}^{\pi} p(\theta) d\theta = 1.$$

The variable $\theta$ is represented as a complex number $e^{i\theta}$ and employs the notation of circular mean direction $\mu_\theta^c$ and circular variance $V_\theta^c$ defined by $$\rho_\theta \exp(i\mu_\theta^c) = E[\exp(i\theta)]$$

with $V_\theta^c = 1 - \rho_\theta$. The quantity $\rho_\theta$ is called the resultant length. Figuratively speaking, $\mu_\theta^c$ is the expected phase and $\rho_\theta$ the expected length of $e^{i\theta}$. $V_\theta^c \in [0,1]$ measures the amount of dispersion. It can be shown that these definitions of mean and variance fulfill the desired shift invariance and can be utilized as suitable counterparts for the linear mean and variance.

A number of models that have been proposed for the statistical modeling of directional data. According to an embodiment of the invention, the multivariate wrapped Gaussian distribution is used, which is an extension of the wrapped Gaussian distribution. A Gaussian distribution $N(x)$ of a variable $x$ on the line can be "wrapped" around the circumference of a circle of unit radius. That is, the wrapped Gaussian distribution $N_w(\theta)$ of the wrapped variable $$\vartheta = x_w = x \mod 2\pi \in (-\pi, \pi]$$

is $$N_w(\vartheta) = \sum_{k=-\infty}^{\infty} N(\vartheta + 2k\pi).$$

Figure 3:
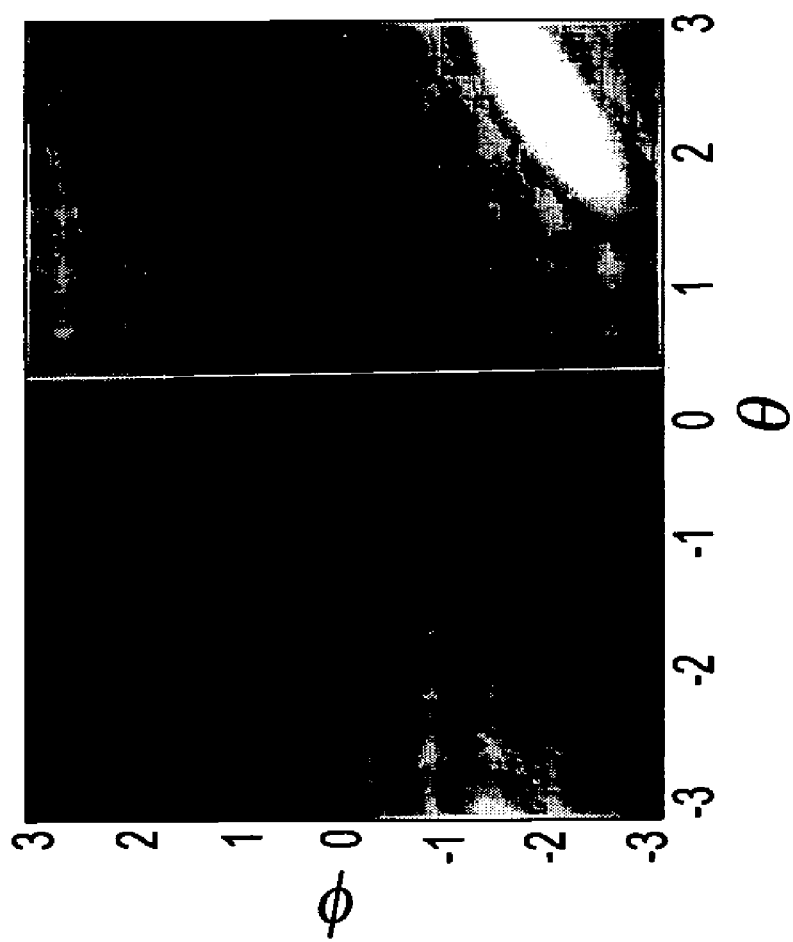
FIG. 3 illustrates clustering with directional data, according to an embodiment of the invention.

A multivariate wrapped Gaussian distribution of a vector variable $\Theta = (\vartheta_1, \ldots, \vartheta_F)^T$ can be defined similarly as $$N_w(\Theta) = \sum_{k_1=-\infty}^{\infty} \ldots \sum_{k_F=-\infty}^{\infty} N(\Theta + 2\pi k_1 e_1 + \ldots + 2\pi k_F e_F), \quad (1)$$

where $e_k = (0, \ldots, 0, 1, 0, \ldots, 0)^T$ is the $k^{th}$ Euclidean basis vector, with an entry of 1 at the $k^{th}$ element and 0 elsewhere. FIG. 3 illustrates an example of a two dimensional multivariate wrapped Gaussian.

It has been shown that, given an appropriately small variance in the directional variables, accurate mean and covariance estimates $\hat{\mu}\vartheta$ and $\hat{\Sigma}\vartheta$ for EQ. (1) can be obtained from a sample set $X = \{\vartheta^{(1)}, \ldots, \vartheta^{(M)}\}$ using $$(\hat{\mu}_\vartheta)_f = \arg\left(\frac{1}{M} \sum_{m=1}^{M} \exp(i\vartheta_f^{(m)})\right) \quad (2)$$

and $$\hat{\Sigma}_\vartheta = \frac{1}{M-1} \sum_{m=1}^{M} \Theta^{(m)'} \Theta^{(m)'T} \quad (3)$$

with $$\vartheta^{(m)'} = \left(\vartheta_f^{(m)} - (\hat{\mu}_\vartheta)_f\right) \mod 2\pi,$$

$i^2 = -1$, and "arg" being the phase of a complex number. For simplicity, a periodicity of $2\pi$ and range of $\vartheta_f \in (-\pi, \pi]$ has implicitly been assumed for all dimensions $f$ in $\Theta$.

An expectation-maximization (EM) algorithm is a class of statistical procedures for finding maximum likelihood estimates of parameters in probabilistic models, where the model depends on unobserved latent variables. EM alternates between performing an expectation (E) step, which computes an expectation of the likelihood by including the latent variables as if they were observed, and a maximization (M) step, which computes the maximum likelihood estimates of the parameters by maximizing the expected likelihood found on the E step. The parameters found on the M step are then used to begin another E step, and the process is repeated. An EM algorithm will iteratively improve an initial estimate $\theta_0$ and construct new estimates $\theta_1, \ldots, \theta_n$.

If y denotes incomplete data consisting of values of observable variables and x denotes the missing data, then x and y together form the complete data set. Let p be the joint probability distribution function of the complete data with parameters given by the vector $\theta$: $p(y, x|\theta)$. This function provides the complete data likelihood. Then, using the Bayes rule, the expectation given the conditional distribution of the unobserved variables is $$p(x|y, \theta) = \frac{p(y, x|\theta)}{p(y|\theta)} = \frac{p(y|x, \theta)p(x|\theta)}{\int p(y|\hat{x}, \theta)p(\hat{x}|\theta)d\hat{x}}.$$

This formulation only requires knowledge of the observation likelihood given the unobservable data $p(y|x, \theta)$, as well as the probability of the unobservable data $p(x|\theta)$. An individual maximization step that derives $\theta_{n+1}$ from $\theta_n$ is:

$$\theta_{n+1} = \arg\max_\theta E_x[\log p(y, x|\theta) | y]$$

where $E_x[\ ]$ denotes the conditional expectation of log $p(y, x|\theta)$ being taken with $\theta$ in the conditional distribution of x fixed at $\theta_n$. The log-likelihood log $p(y,x|\theta)$ is often used instead of true likelihood $p(y,x|\theta)$ because it leads to easier formulas, but still attains its maximum at the same point as the likelihood. In other words, $\theta_{n+1}$ is the value that maximizes (M) the conditional expectation (E) of the complete data log-likelihood given the observed variables under the previous parameter value. Typically, the maximum is found by forming a Lagrangian function of the log-likelihood, and then evaluating derivatives with respect to the mean and covariance.

In the context of the EM clustering algorithm, the regular, linear Gaussian model can be replaced with the above sketched multivariate wrapped Gaussian model. In particular, EQ. (1) on the one hand and EQS. (2) and (3) on the other hand replace the original linear equivalents in the E and the M step, respectively.

According to an embodiment of the invention, a model for mode number selection can be found from a modified EM clustering algorithm that uses a finite mixture of Gaussian estimation and model selections subject to a minimum description length (MDL) criterion to minimize the number of components in the mixture. In general, the input to an EM clustering algorithms is a sample set $X=\{(\theta_1, \phi_1), \ldots, (\theta_M, \phi_M)\}$ of observations, whereas the present data is the 2D (image) matrix $I(\theta, \phi)$. To overcome this incompatibility, observations X are drawn directly from $I(\theta, \phi)$, where the number of occurrences of each sampled $(\theta_m, \phi_m) \in (-\pi, \pi] \times (-\pi, \pi]$ is set proportional to the corresponding image matrix value $I(\theta_m, \phi_m)$.

One concern with the Gaussian EM clustering arises when one of the true protruding structure shapes in the bounding manifold does not correspond to the elliptical Gaussian shape. In such cases, it is expected that the EM algorithm fits this structure with a set of Gaussian components. Such an effect would clearly affect the classification adversely, where the number of components plays an integral role.

Referring again to FIG. 7, according to an embodiment of the invention, post-processing is applied at step 76 to merge appropriate components. In particular, this post-processing of an embodiment of the invention can be seen as a second cluster analysis, which analyzes the set of all EM-fitted Gaussian components and merges subsets to a single cluster, up to a certain scale. One technique well known in the art for such situations is agglomerative hierarchical clustering. In hierarchical clustering, the cluster space is expressed in terms of distances of its elements. In the present case the elements are multivariate wrapped Gaussian functions, and statistical descriptors are used for the geometric shapes. A suitable (and analytically computable) statistical distance measure for Gaussian distributions is the Bhattacharyya distance $$D_{Bhatt}(\mu_1, \Sigma_1, \mu_2, \Sigma_2) = \frac{1}{8}(\mu_2 - \mu_1)^T \left(\frac{\Sigma_1 + \Sigma_2}{2}\right)^{-1}(\mu_2 - \mu_1) + \frac{1}{2}\ln\frac{|\Sigma_1 + \Sigma_2|}{\sqrt{|\Sigma_1||\Sigma_2|}}$$

However, $D_{Bhatt}$ does not take into account the directional characteristics of the wrapped Gaussians. Hence, according to an embodiment of the invention, modified variant of $D_{Bhatt}$ is proposed, the "wrapped Bhattacharyya distance":

$$D^w_{Bhatt}(\mu_1, \Sigma_1, \mu_2, \Sigma_2) =$$
$$\frac{1}{8}((\mu_2 - \mu_1)\bmod 2\pi)^T\left(\frac{\Sigma_1 + \Sigma_2}{2}\right)^{-1}((\mu_2 - \mu_1)\bmod 2\pi) + \frac{1}{2}\ln\frac{|\Sigma_1 + \Sigma_2|}{\sqrt{|\Sigma_1||\Sigma_2|}}$$

Finally, the number of wrapped Gaussian component clusters determines the class of the pulmonary structure: 0 for a solitary nodule, $2\times1=2$ for an attached nodule, $2\times2=4$ for a vessel, and $>2\times3=6$ for vessel junction. The factor of 2 is due to the double interval in the polar coordinate A, as discussed above.

A limitation of the method of an embodiment of the invention is the fact that scales are position dependent within the $(\theta, \phi)$-domain. One alternative according to an embodiment of the invention would be modeling the directional data with von Mises-Fisher distribution could circumvent this problem. The von Mises-Fisher distribution for a d-dimensional unit random vector takes the form $$f(x|\mu, \kappa) = c_d(\kappa)\exp(\kappa\mu^T x),$$

where $\|\mu\|=1$, $\kappa \geq 0$, and $d \geq 2$. The normalizing constant $c_d(\kappa)$ is given by $$c_d(\kappa) = \frac{\kappa^{d/2-1}}{(2\pi)^{d/2}I_{d/2-1}(\kappa)},$$

where $I_r(\ )$ represents a modified Bessel function of the first kind of order r. The distribution is parameterized by the mean direction $\mu$ and concentration parameter $\kappa$, which characterizes how strongly the unit vectors drawn according to $f(x|\mu, \kappa)$ are concentrated about the means direction $\mu$. However, parameter estimation for the von Mises-Fisher distribution involves solving an implicit equation of a ratio of Bessel functions, for which no analytic solution exists, in general.

Figures 4A, 4B:
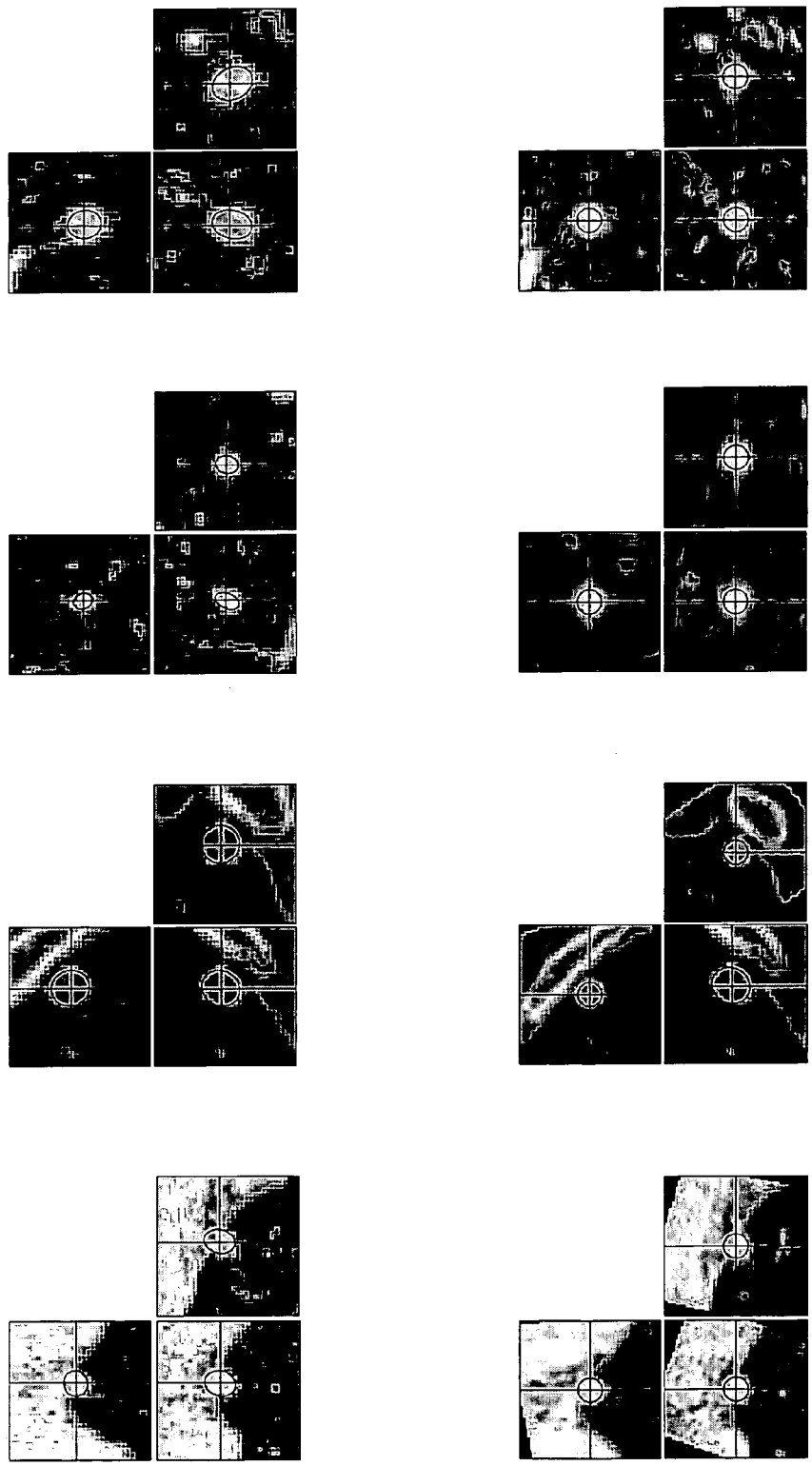
Figures 5A, 5B:
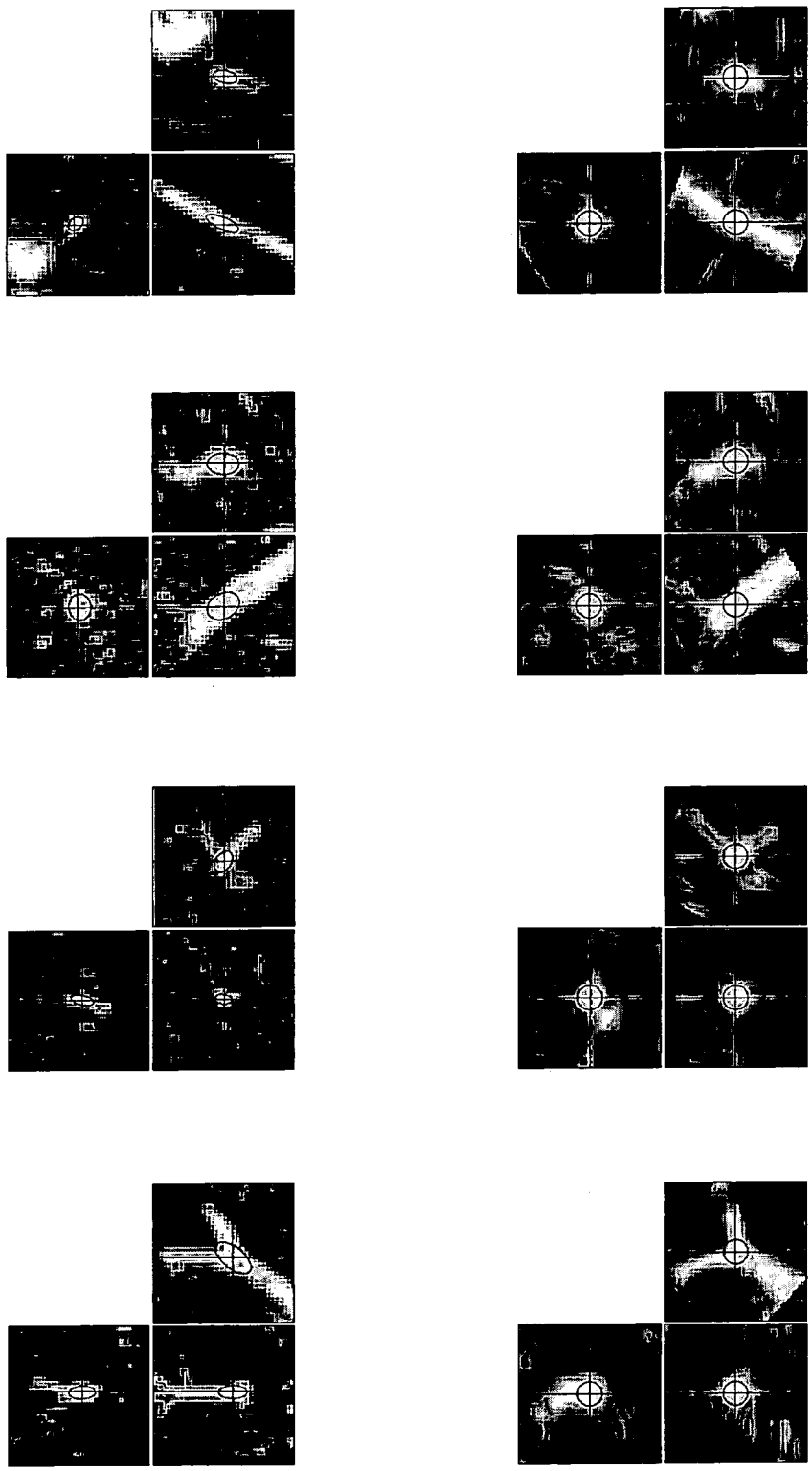

According to an embodiment of the invention, qualitative experiments were performed for the proposed pulmonary structure classification. FIGS. 4 and 5 show illustrations of the classification for thoracic CT images, two examples for each of the classes "nodule", "attached nodule", "vessel", "vessel junction".

FIGS. 4(a)-(d) and 5(a)-(d) depict illustrative examples of a pulmonary structure classification method of an embodiment of the invention for thoracic CT scans. Each row corresponds to the segmentation and verification of one example. The first two rows of FIG. 4 are with respect to a nodule object, the last two rows are with respect to nodules attached to the lung wall, while rows 1 and 2 of FIG. 5 show vascular structures, and rows 3 and 4 vessel junctions. Column (a) illustrates the CT VOI in three orthogonal cross sections. The segmentation result is illustrated by the ellipses. Column (b) represents the affine-normalization of the original VOI, such that the 3D ellipsoid becomes warped into a sphere. Column (c) shows the constructed bounding manifold unwrapped in the $(\theta, \phi)$-domain. Note, however, that an additional intensity thresholding has been introduced. This step is applied as a fast and simple means for eliminating low-intensity structures, which may confuse the Gaussian EM clustering. The figures in column (d) show the results of the Gaussian mixture model fitting by the EM-based algorithm. Dashed ellipses correspond to EM-based clustered Gaussian components, and solid ellipses describe the clusters after post-processing.

As presented in Column (a), the 3D segmentation can segment all solitary and attached nodules, as shown in FIG. 4, as well as the false positive blood vessels and vessel junctions, as shown in FIG. 5. In column (d) the bounding manifold image is transformed to a sampled data set X, as it has been described in Section 2.2.1. Further, column (d) shows the result of the EM-based wrapped Gaussian clustering, that is, mean and covariance of the k components are illustrated by the dashed ellipses. In particular, note the continuities at the edges of the $(\theta, \phi)$-domain in FIG. 4, row 3 and 4, and FIG. 5, row 3 and 4. For visualization purposes, an illustration of the hierarchical clustering post-processing has been included. Clusters from this post-processing are represented by the $k_2$ solid ellipses, the center point and spread of which correspond to mean and covariance computed from means of all wrapped Gaussians within one post-processed cluster. Note that this illustration may lead to degenerated ellipses, for instance in FIG. 5, row 2, if the cluster cardinality is low. Inferring the structure class from the component number $k_2$, it can be verified that the presented classification gives correct answer for all eight examples. Similar results were obtained with other cases.

It is worthwhile to point out limitations of the classification, which may lead to misclassifications in some situations. Structures at the poles of the manifold 3D sphere (corresponding to $\theta=0$ and $\phi=\pi$) become disproportionately large in the $\theta$-dimension of the 2D image after the unwrapping. This situation can be compared with a phenomenon from cartography where arctic and antarctic regions occupy comparably larger regions on a 2D Mercator projection world map than on the 3D spherical world globe. In the examples illustrated above, this behavior can be observed in FIG. 5, row 4, where the high intensity structure at $\phi \approx \pi$ extends over the entire range $(-\pi, \pi]$ in $\theta$. As a consequence, caution is advised, when drawing conclusions from scale relations in the unwrapped manifold, in particular, for those pole regions. This is, in fact, a drawback of the wrapped Gaussian modeling, in particular, the unwrapping. At this point, it shall be noted that a von Mises-Fisher modeling circumvents this phenomenon, because no unwrapping is assumed.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 8:
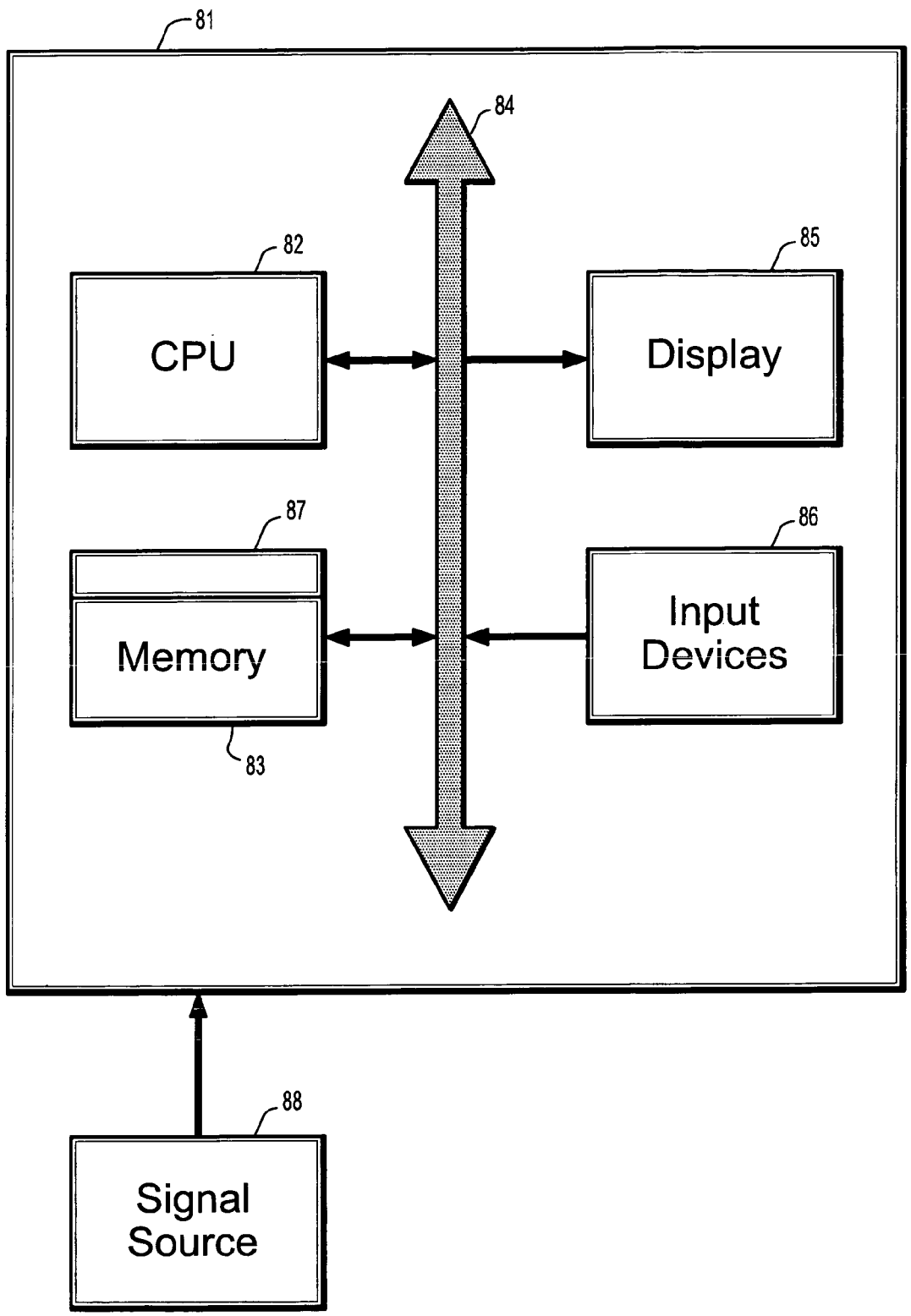
FIG. 8 is a block diagram of an exemplary computer system for implementing a classification method according to an embodiment of the invention.

FIG. 8 is a block diagram of an exemplary computer system for implementing a classification method according to an embodiment of the invention. Referring now to FIG. 8, a computer system 81 for implementing the present invention can comprise, inter alia, a central processing unit (CPU) 82, a memory 83 and an input/output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present invention can be implemented as a routine 87 that is stored in memory 83 and executed by the CPU 82 to process the signal from the signal source 88. As such, the computer system 81 is a general purpose computer system that becomes a specific purpose computer system when executing the routine 87 of the present invention.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for classifying pulmonary structures in digitized images, comprising the steps of:
   providing approximate target structure locations of one or more target structures in a digitized 3-dimensional (3D) image;
   fitting an anisotropic Gaussian model about said approximate target locations to generate more precise 3D target models and center locations of said one or more target structures;
   warping each said 3D target models into a 3D sphere;
   constructing a bounding manifold about each said warped 3D sphere; and
   identifying clusters on said bounding manifolds wherein said one or more target structures are classified.

2. The method of claim 1, wherein said digitized image comprises a plurality of intensities corresponding to a domain of points on a 3-dimensional grid.

3. The method of claim 1, wherein fitting an anisotropic Gaussian model about an approximate target location comprises using Gaussian scale-space mean shift analysis and Jensen-Shannon divergence-based automatic bandwidth selection generating a 3D ellipsoidal model of said target structure, wherein the center and dimensions of said 3D ellipsoid correspond to the center and covariances of said Gaussian model.

4. The method of claim 3, wherein warping said 3D target model comprises affine-normalizing said 3D ellipsoid wherein scaling directions and factors are obtained from the structure covariance of said anisotropic Gaussian model.

5. The method of claim 1, wherein constructing a bounding manifold further comprises unwrapping the 3D surface of the warped sphere into a 2D representation, and determining a radius of an appropriate bounding manifold.

6. The method of claim 5, wherein unwrapping the 3D surface of the warped sphere into a 2D representation comprises transforming the surface of said warped sphere into spherical coordinates $(\theta, \phi)$ wherein $\phi \in [-\pi, \pi]$ and $\theta \in -\pi, \pi]$.

7. The method of claim 5, wherein determining a radius of an appropriate bounding manifold comprises constructing a plurality of spherical manifolds of different radii about said warped sphere, unwrapping each spherical manifold into a 2D representation, normalizing the intensity value distribution on each said unwrapped spherical manifold, calculating an intensity entropy for each said unwrapped spherical manifold wherein intensity values are treated as probability values wherein an entropy distribution is defined, and finding a radius that minimizes said entropy distribution.

8. The method of claim 1, wherein identifying clusters comprises using an expectation-maximization to fit a mixture $$N_w(\Theta) = \sum_{p=1}^{P} c_p N_w^p(\Theta)$$

of multivariate wrapped Gaussian distributions $N_w^p(\Theta)$ of a vector variable $\Theta = (\vartheta_1, \ldots, \vartheta_F)^T$ to objects protruding through said bounding manifold subject to a minimum description length criterion, wherein mixture component probabilities $c_p$ are estimated within the expectation-maximization, wherein in each dimension $\vartheta_i$ satisfies $\vartheta = x_w = x \mod 2\pi \in (-\pi, \pi]$, $N_w^p(\Theta)$ satisfies $$N_w^p(\Theta) = \sum_{k_1=-\infty}^{\infty} \cdots \sum_{k_F=-\infty}^{\infty} N^p(\Theta + 2\pi k_1 e_1 + \ldots + 2\pi k_F e_F),$$

wherein $e_k = (0, \ldots, 0, 1, 0, \ldots, 0)^T$ is the $k^{th}$ Euclidean basis vector, with an entry of 1 at the $k^{th}$ element and 0 elsewhere, wherein estimates $\hat{\mu}_\theta^p$ and $\hat{\Sigma}_\theta^p$ of a mixture component p are obtained within the expectation-maximization from a sample set $X = \{\vartheta^{(1)}, \ldots, \vartheta^{(M)}\}$ based on a directional mean $$(\hat{\mu}_\theta)_f = \arg\left(\frac{1}{M}\sum_{m=1}^{M} \exp(i\vartheta_f^{(m)})\right)$$

and covariance $$\hat{\Sigma}_\theta = \frac{1}{M-1}\sum_{m=1}^{M} \Theta^{(m)'}\Theta^{(m)'T}$$

with $\vartheta^{(m)'} = (\vartheta_f^{(m)} - (\hat{\mu}\vartheta)_f) \mod 2\pi$, and wherein observations X are drawn directly from a 2D unwrapped image $I(\theta, \phi)$, where the number of occurrences of each sampled $(\theta_m, \phi_m) \in (-\pi, \pi] \times (-\pi, \pi]$ is set proportional to a corresponding image matrix value $I(\theta_m, \phi_m)$.

9. The method of claim 1, further comprising using agglomerative hierarchical clustering to merge clusters within a predefined distance of each other, using a distance metric for a pair of multivariate wrapped Gaussian distributions equivalent to $$\frac{1}{8}((\mu_2 - \mu_1)\mod 2\pi)^T \left(\frac{\Sigma_1 + \Sigma_2}{2}\right)^{-1}((\mu_2 - \mu_1)\mod 2\pi) + \frac{1}{2}\ln\frac{|\Sigma_1 + \Sigma_2|}{\sqrt{|\Sigma_1||\Sigma_2|}},$$

wherein $\mu_1$ and $\mu_2$ are the mean values of the pair of Gaussian distributions, and $\Sigma_1$ and $\Sigma_2$ are their respective variances.

10. The method of claim 1, wherein the pulmonary structure class is determined by the number of wrapped Gaussian component clusters associated with a target structure, wherein a solitary nodule has 0 clusters, an attached nodule has 2 clusters, a vessel has 4 clusters, and a vessel junction has 6 or more clusters.

11. A method for classifying pulmonary structures in digitized images, comprising the steps of:
    providing target locations of one or more 3D spheres in a digitized 3-dimensional (3D) image, said image comprising a plurality of intensities corresponding to a domain of points on a 3-dimensional grid, each 3D sphere representing a target structure in said image;
    constructing a plurality of spherical manifolds of different radii about said 3D sphere;
    calculating an intensity entropy for each said spherical manifold wherein intensity values are treated as probability values wherein an entropy distribution is defined;
    finding a radius that minimizes said entropy distribution, wherein said minimizing radius defines a bounding manifold;
    unwrapping the surface of bounding manifold into a 2D spherical coordinate $(\theta, \phi)$ representation wherein $\phi \in [-\pi, \pi]$ and $\theta \in [-\pi, \pi]$;
    using expectation-maximization to fit a mixture $$N_w(\Theta) = \sum_{p=1}^{P} c_p N_w^p(\Theta)$$

of multivariate wrapped Gaussian distribution $N_w(\Theta)$ of a vector variable $\Theta = (\vartheta_1, \ldots, \vartheta_F)^T$, wherein mixture component probabilities $c_p$ are estimated within the expectation-maximization, wherein $\vartheta_i = (\theta_i, \phi_i)$ to clusters of target structures protruding through said bounding manifold, and wherein a pulmonary structure is classified by a number of protruding clusters.

12. The method of claim 11, further comprising normalizing the intensity distribution on each of said plurality of spherical manifolds.

13. The method of claim 11, wherein providing target locations of one or more 3D sphere comprises providing approximate target structure locations of said one or more target structures in said digitized 3-dimensional (3D) image; fitting an anisotropic Gaussian model about said approximate target locations to generate more precise 3D ellipsoidal target models and center locations of said ellipsoidal models; and affine-normalizing said ellipsoidal models into a 3D sphere.

14. The method of claim 11, wherein in each dimension $\vartheta_i$ satisfies $\vartheta = x_w = x \mod 2\pi \in (-\pi, \pi]$, $N_w(\Theta)$ satisfies $$N_w(\Theta) = \sum_{k_1=-\infty}^{\infty} \cdots \sum_{k_F=-\infty}^{\infty} N(\Theta + 2\pi k_1 e_1 + \ldots + 2\pi k_F e_F),$$

wherein $e_k = (0, \ldots, 0, 1, 0, \ldots, 0)^T$ is the $k^{th}$ Euclidean basis vector, with an entry of 1 at the $k^{th}$ element and 0 elsewhere, wherein estimates $\hat{\mu}\vartheta$ and $\hat{\Sigma}\vartheta$ of a mixture component p are obtained within the expectation-maximization from a sample set $X = \{\vartheta^{(1)}, \ldots, \vartheta^{(M)}\}$ based on a directional mean $$(\hat{\mu}_\theta)_f = \arg\left(\frac{1}{M}\sum_{m=1}^{M} \exp(i\vartheta_f^{(m)})\right)$$

and covariance $$\hat{\Sigma}_\vartheta = \frac{1}{M-1}\sum_{m=1}^{M} \Theta^{(m)'}\Theta^{(m)'T}$$

with $\vartheta^{(m)'} = (\vartheta_f^{(m)} - (\hat{\mu}\vartheta)_f) \mod 2\pi$, and wherein observations X are drawn directly from a 2D unwrapped image $I(\theta, \phi)$, where the number of occurrences of each sampled $(\theta_m, \phi_m) \in (-\pi, \pi] \times (-\pi, \pi]$ is set proportional to a corresponding image matrix value $I(\theta_m, \phi_m)$.

15. A program storage device readable by a computer, tangibly embodying a program of instructions executable by the computer to perform the method steps for classifying pulmonary structures in digitized images, said method comprising the steps of:
    providing approximate target structure locations of one or more target structures in a digitized 3-dimensional (3D) image;

fitting an anisotropic Gaussian model about said approximate target locations to generate more precise 3D target models and center locations of said one or more target structures;
warping each said 3D target model into a 3D sphere;
constructing a bounding manifold about each said warped 3D sphere; and
identifying clusters on said bounding manifold wherein said one or more target structures are classified.

16. The computer readable program storage device of claim 15, wherein said digitized image comprises a plurality of intensities corresponding to a domain of points on a 3-dimensional grid.

17. The computer readable program storage device of claim 15, wherein fitting an anisotropic Gaussian model about an approximate target location comprises using Gaussian scale-space mean shift analysis and Jensen-Shannon divergence-based automatic bandwidth selection generating a 3D ellipsoidal model of said target structure, wherein the center and dimensions of said 3D ellipsoid correspond to the center and covariances of said Gaussian model.

18. The computer readable program storage device of claim 17, wherein warping said 3D target model comprises affine-normalizing said 3D ellipsoid wherein scaling directions and factors are obtained from the structure covariance of said anisotropic Gaussian model.

19. The computer readable program storage device of claim 15, wherein constructing a bounding manifold further comprises unwrapping the 3D surface of the warped sphere into a 2D representation, and determining a radius of an appropriate bounding manifold.

20. The computer readable program storage device of claim 19, wherein unwrapping the 3D surface of the warped sphere into a 2D representation comprises transforming the surface of said warped sphere into spherical coordinates $(\theta, \phi)$ wherein $\phi \in [-\pi, \pi]$ and $\theta \in [-\pi, \pi]$.

21. The computer readable program storage device of claim 19, wherein determining a radius of an appropriate bounding manifold comprises constructing a plurality of spherical manifolds of different radii about said warped sphere, unwrapping each spherical manifold into a 2D representation, normalizing the intensity value distribution on each said unwrapped spherical manifold, calculating an intensity entropy for each said unwrapped spherical manifold wherein intensity values are treated as probability values wherein an entropy distribution is defined, and finding a radius that minimizes said entropy distribution.

22. The computer readable program storage device of claim 15, wherein identifying clusters comprises using an expectation-maximization to fit a mixture $$N_w(\Theta) = \sum_{p=1}^{P} c_p N_w^p(\Theta)$$

of multivariate wrapped Gaussian distributions $N_w^p(\Theta)$ of a vector variable $\Theta = (\vartheta_1, \ldots, \vartheta_F)^T$ to objects protruding through said bounding manifold subject to a minimum description length criterion, wherein mixture component probabilities $c_p$ are estimated within the expectation-maximization, wherein in each dimension $\vartheta_i$ satisfies $\vartheta = x_w = x \mod 2\pi \in (-\pi, \pi]$, $N_w^p(\Theta)$ satisfies $$N_w^p(\Theta) = \sum_{k_1=-\infty}^{\infty} \cdots \sum_{k_F=-\infty}^{\infty} N^p(\Theta + 2\pi k_1 e_1 + \ldots + 2\pi k_F e_F),$$

wherein $e_k = (0, \ldots, 0, 1, 0, \ldots, 0)^T$ is the $k^{th}$ Euclidean basis vector, with an entry of 1 at the $k^{th}$ element and 0 elsewhere, wherein estimates $\hat{\mu}_\theta^p$ and $\hat{\Sigma}_\theta^p$ of a mixture component p are obtained within the expectation-maximization from a sample set $X = \{\vartheta^{(1)}, \ldots, \vartheta^{(M)}\}$ based on a directional mean $$(\hat{\mu}_\theta)_f = \arg\left(\frac{1}{M}\sum_{m=1}^{M} \exp(i\vartheta_f^{(m)})\right)$$

and covariance $$\hat{\Sigma}_\theta = \frac{1}{M-1}\sum_{m=1}^{M} \Theta^{(m)'}\Theta^{(m)'^T}$$

with $\vartheta^{(m)'} = (\vartheta_f^{(m)} - (\hat{\mu}\vartheta)_f) \mod 2\pi$, and wherein observations X are drawn directly from a 2D unwrapped image $I(\theta, \phi)$, where the number of occurrences of each sampled $(\theta_m, \phi_m) \in (-\pi, \pi] \times (-\pi, \pi]$ is set proportional to a corresponding image matrix value $I(\theta_m, \phi_m)$.

23. The computer readable program storage device of claim 15, the method further comprising using agglomerative hierarchical clustering to merge clusters within a predefined distance of each other, using a distance metric for a pair of multivariate wrapped Gaussian distributions equivalent to $$\frac{1}{8}((\mu_2 - \mu_1)\mod 2\pi)^T \left(\frac{\Sigma_1 + \Sigma_2}{2}\right)^{-1}((\mu_2 - \mu_1)\mod 2\pi) + \frac{1}{2}\ln\frac{|\Sigma_1 + \Sigma_2|}{\sqrt{|\Sigma_1||\Sigma_2|}},$$

wherein $\mu_1$ and $\mu_2$ are the mean values of the pair of Gaussian distributions, and $\Sigma_1$ and $\Sigma_2$ are their respective variances.

24. The computer readable program storage device of claim 15, wherein the pulmonary structure class is determined by the number of wrapped Gaussian component clusters associated with a target structure, wherein a solitary nodule has 0 clusters, an attached nodule has 2 clusters, a vessel has 4 clusters, and a vessel junction has 6 or more clusters.

* * * * *